United States Patent
Zhang et al.

(10) Patent No.: US 11,771,679 B2
(45) Date of Patent: Oct. 3, 2023

(54) COMPOSITION CONTAINING HESPERETIN AND SYNERGISTIC HYPOGLYCEMIC APPLICATION THEREOF

(71) Applicant: ZHENGZHOU FRUIT RESEARCH INSTITUTE, CHINESE ACADEMY OF AGRICULTURAL SCIENCES, Zhengzhou (CN)

(72) Inventors: Qiang Zhang, Zhengzhou (CN); Zhonggao Jiao, Zhengzhou (CN); Dalei Chen, Zhengzhou (CN); Jiechao Liu, Zhengzhou (CN); Wenbo Yang, Zhengzhou (CN); Chunling Zhang, Zhengzhou (CN); Hui Liu, Zhengzhou (CN); Zhenzhen Lv, Zhengzhou (CN); Junkun Pan, Zhengzhou (CN)

(73) Assignee: ZHENGZHOU FRUIT RESEARCH INSTITUTE, CHINESE ACADEMY OF AGRICULTURAL SCIENCES, Henan (CN)

( * ) Notice: Subject to any disclaimer, the term of this patent is extended or adjusted under 35 U.S.C. 154(b) by 0 days.

(21) Appl. No.: 18/081,954

(22) Filed: Dec. 15, 2022

(65) Prior Publication Data
US 2023/0125518 A1    Apr. 27, 2023

Related U.S. Application Data

(63) Continuation of application No. PCT/CN2022/111358, filed on Aug. 10, 2022.

(30) Foreign Application Priority Data

Aug. 20, 2021 (CN) .......................... 202110960281.5

(51) Int. Cl.
   *A61K 31/352*  (2006.01)
   *A61P 3/10*  (2006.01)

(52) U.S. Cl.
   CPC .............. *A61K 31/352* (2013.01); *A61P 3/10* (2018.01)

(58) Field of Classification Search
   CPC .............. A61K 31/352; A61K 2300/00; A61K 31/353; A61K 31/7048; A61P 3/10
   (Continued)

(56) References Cited

U.S. PATENT DOCUMENTS

2018/0296490 A1    10/2018    Nitin et al.

FOREIGN PATENT DOCUMENTS

| CN | 106924239 A | 7/2017 |
| CN | 109475757 A * | 3/2019 |

(Continued)

OTHER PUBLICATIONS

Brand et al ,The effect of co-administered flavonoids on the metabolism of hesperetin and the disposition of its metabolites in Caco-2 cell monolayers, Mol. Nutr. Food Res. 2010, 54, 851-860). (Year: 2010).*

(Continued)

*Primary Examiner* — Taylor V Oh
(74) *Attorney, Agent, or Firm* — SZDC Law PC

(57) ABSTRACT

The present invention discloses a composition containing hesperetin and synergistic hypoglycemic application thereof, and belongs to the technical field of natural active compounds. The composition of the present invention contains the hesperetin and a compound X, and the compound X is galangin or formononetin, where a mass ratio of the hesperetin to the galangin is 30:100, and a mass ratio of the hesperetin to the formononetin is 30:20. The composition of the present invention has an obvious synergistic effect of inhibiting α-glucosidase, and the effect thereof is better than (Continued)

that of using the flavonoid compound alone, and may reduce a dosage of the use of drugs and occurrence of drug resistance.

6 Claims, 13 Drawing Sheets

(58) Field of Classification Search
USPC .......................................................... 514/456
See application file for complete search history.

(56) References Cited

FOREIGN PATENT DOCUMENTS

| | | |
|---|---|---|
| CN | 111388461 A | 7/2020 |
| CN | 113440514 A | 9/2021 |
| WO | 2010129138 A1 | 11/2010 |

OTHER PUBLICATIONS

Fengyi Gao et al., "Effects of Different Dietary Flavonoids on Dipeptidyl Peptidase-IV Activity and Expression: Insights into Structure-Activity Relationship" J. Agric. Food Chem. 2020, 68, 12141-12151 (Oct. 16, 2020).

J Ma et al. "Inhibitory Effect of Pueraria Isoflavones on α-Glucosidase and Structure-Effect Analysis" Chinese Traditional Patent Medicine, vol. 37, No. 4, pp. 858-862 (Apr. 20, 2015).

Li Zeng et al. "Galangin inhibits α-glucosidase activity and formation of non-enzymatic glycation products" Food Chem. No. 2712, pp. 70-79 (Jan. 15, 2019).

\* cited by examiner

COMPOSITION CONTAINING HESPERETIN AND SYNERGISTIC HYPOGLYCEMIC APPLICATION THEREOF

This application is a Continuation Application of PCT/CN2022/111358, filed on Aug. 10, 2022, which claims priority to Chinese Patent Application No. 202110960281.5, filed on Aug. 20, 2021, which is incorporated by reference for all purposes as if fully set forth herein.

TECHNICAL FIELD

The present invention belongs to the technical field of natural active compounds, and in particular, relates to a composition containing hesperetin and synergistic hypoglycemic application thereof.

BACKGROUND

Diabetes is a global chronic disease characterized by persistent hyperglycemia, including type I, type II diabetes, gestational diabetes and other special types of diabetes, where the type II diabetes is also referred to as non-insulin dependent diabetes, accounting for more than 95% of diabetes patients. α-glucosidase is a carbohydrate hydrolase and catalyzes the release of α-glucose from a non-reducing end of substrate. The α-glucosidase exists in most microorganisms, plants and animals and is an indispensable enzyme in the pathway of starch being metabolized to generate glucose. When the activity of the α-glucosidase in a human body is too high, blood glucose in the body will be too high, thereby leading to diabetes. At present, commonly used drugs to treat diabetes in clinic include insulin, sulfonylureas, biguanides, thiazolidinediones and α-glucosidase inhibitors, but long-term use will cause hypoglycemia, abdominal pain, vomiting, diarrhea and other side effects. The α-glucosidase inhibitor can delay absorption of carbohydrates by competitively inhibiting the activity of the α-glucosidase, thereby lowering postprandial and fasting blood glucose levels. Natural α-glucosidase inhibitors are green and safe, have little toxic side effects, and have other features and are a research focus in the fields of medicine, pharmacy, and functional food. Many domestic and foreign researchers devote themselves to the research on extraction, purification, and separation and identification of the α-glucosidase inhibitors in plant resources, aiming to develop drugs that are new and efficient, and have no toxic side effects and are used for treating diabetes and complications thereof. For example, polyphenolic compounds such as flavonoid, phenolic acid and tannin are common components for inhibiting the activity of the α-glucosidase in the plant resources.

Combination refers to simultaneous or sequential application of two or more drugs for a purpose of treatment, and a result thereof is mainly to increase drug treatment or reduce the toxic side effects of the drugs, but sometimes opposite results may be generated. Therefore, combination rationality should be based on the basic principles of improving efficacy and(or) reducing adverse reactions. If compatibility of the two drugs generates a synergistic effect, a therapeutic effect of the two drugs may be significantly improved compared with the use of a single drug. At present, most of the studies on the α-glucosidase inhibitors focus on single compounds, and continuous use will produce certain side effects and tolerance, while there are few reports on synergistic effect between active molecules. Therefore, it is of great significance to study the combination of flavonoid compounds to inhibit the α-glucosidase and improve hypoglycemic activity for improving human health.

SUMMARY

The purpose of the present invention is to provide a composition containing hesperetin and synergistic hypoglycemic application thereof, to solve a problem that hypoglycemic effect of a single active component in the prior art is limited and it is easy to produce drug resistance.

In order to achieve the above purpose, the present invention is implemented by the following technical solutions:
a composition containing hesperetin, where the composition contains the hesperetin and a compound X; the compound X is galangin or formononetin,
a mass ratio of the hesperetin to the galangin is 30:100; and a mass ratio of the hesperetin to the formononetin is 30:20.

Application of the above composition in the preparation of a formulation having an effect of inhibiting α-glucosidase.

An α-glucosidase inhibitor, where effective components thereof contain hesperetin and galangin or hesperetin and formononetin; a mass ratio of the hesperetin to the galangin is 30:100; and a mass ratio of the hesperetin to the formononetin is 30:20.

Application of the above composition in the preparation of a drug having a hypoglycemic effect, where the hypoglycemic effect is to block digestion and absorption of carbohydrates by inhibiting activity of α-glucosidase to achieve a purpose of controlling postprandial hyperglycemia.

A drug having a hypoglycemic effect, where effective components thereof contains hesperetin and galangin or hesperetin and formononetin; a mass ratio of the hesperetin to the galangin is 30:100; and a mass ratio of the hesperetin to the formononetin is 30:20.

In a limited mass concentration ratio range, the hesperetin and galangin and the hesperetin and formononetin achieve synergistic technical effect.

The drug in the present invention contains a carrier, a solvent, a diluent, and an excipient acceptable in pharmacy that are mixed with other mediums, and may be prepared into powder, granules, capsules, injection, oral liquid, or tablets according to different demands.

Advantages of the technical solutions of the present invention:

according to the present invention, the composition of the hesperetin and the galangin and the composition of the hesperetin and the formononetin have an obvious synergistic effect of inhibiting α-glucosidase, and the effect thereof is better than that of using the flavonoid compound alone, and may reduce a dosage of the use of drugs and occurrence of drug resistance. When the formononetin or the galangin is replaced with genistein with a similar chemical structure, the synergistic effect disappears.

By means of an external inhibition test for the α-glucosidase and using a Chou-Talalay method, it is proved that when the composition of the hesperetin and the galangin and the composition of the hesperetin and the formononetin respectively have an obvious synergistic effect on the α-glucosidase at mass ratios of 30:100 and 30:20, CI values when inhibition rates are at 50% ($GI_{50}$), 75% ($GI_{75}$), and 90%

($GI_{90}$) are less than 1.0, the synergistic effect between drugs at a high inhibition rate is generally stronger than that at a low inhibition rate.

DETAILED DESCRIPTION OF THE EMBODIMENTS

Figure 1:
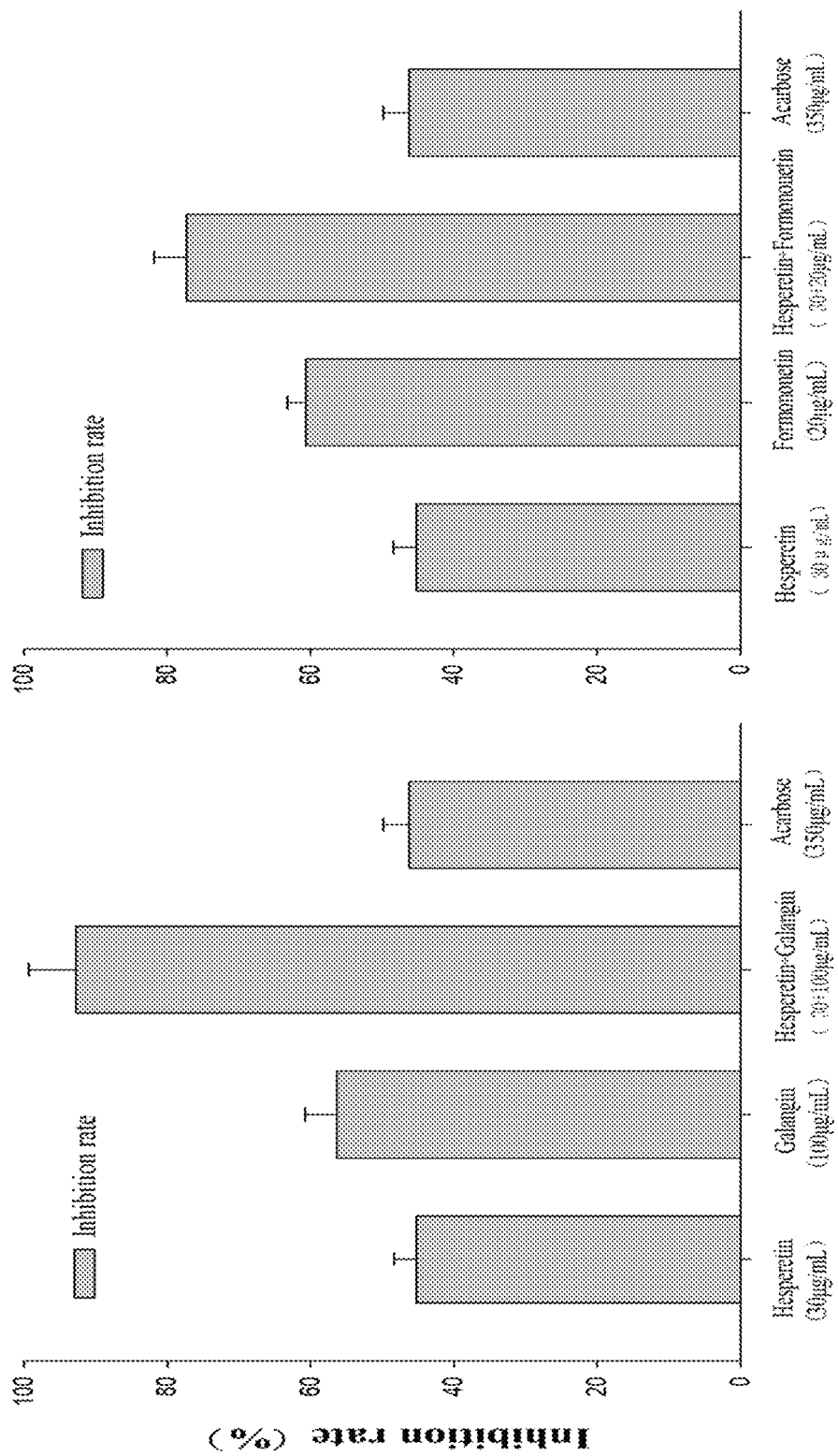
FIG. 1 shows inhibitory activity of a hesperetin composition in Embodiment 1 and Embodiment 4 on α-glucosidase.

The terms used in the present invention, unless otherwise specified, generally have meanings normally understood by those of ordinary skills in the art.

Hesperetin: a molecular formula is $C_{16}H_{14}O_6$; a molecular weight is: 302.28; a CAS accession number is: 520-33-2; and a structural formula is:

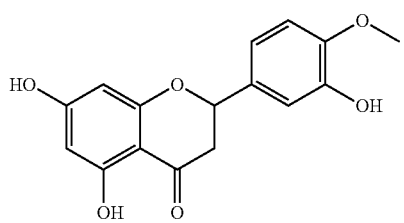 [SMILES: COc1ccc(C2CC(=O)c3c(O)cc(O)cc3O2)cc1O]

Galangin: a molecular formula is $C_{15}H_{10}O_5$; a molecular weight is: 270.24; a CAS accession number is: 548-83-4; and a structural formula is:

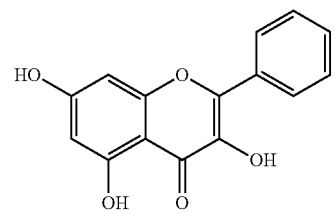 [SMILES: O=c1c(O)c(-c2ccccc2)oc2cc(O)cc(O)c12]

Formononetin: a molecular formula is $C_{16}H_{12}O_4$; a molecular weight is: 268.26; a CAS accession number is: 485-72-3; and a structural formula is:

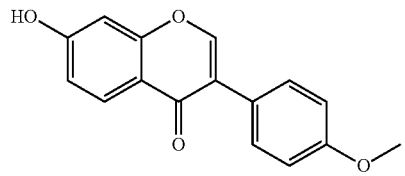 [SMILES: COc1ccc(-c2coc3cc(O)ccc3c2=O)cc1]

α-glucosidase (coming from *Saccharomyces cerevisiae*, Sigma);
4-nitrophenyl-α-D-glucopyranoside (pNPG, TOKYO Chemica Industry Co., LTD);
acarbose (Acarbose, TOKYO Chemica Industry Co., LTD);
hesperetin, galangin, and formononetin (BEIJING Solarbio Technology Co., LTD);
Millipore Simplicity water purification system (Millipore, France);
sodium phosphate salt buffer solution (pH 6.8, 0.1 mol L-1); and
microplate reader TECAN infinite M200 PRO (Teacan Group Ltd., Swizerland).

The present invention will be described in further detail in conjunction with specific embodiments and with reference to data. The following examples are intended only to illustrate the present invention and are not intended to limit the scope of the present invention in any way.

Embodiment 1

A composition of hesperetin and galangin, where a mass ratio of the hesperetin and the galangin is 30:100, and specifically, concentrations of the hesperetin and the galangin in the composition respectively are 30 μg/mL and 100 μg/mL.

Embodiment 2

A composition of hesperetin and galangin, where a mass ratio of the hesperetin and the galangin is 30:150, and specifically, concentrations of the hesperetin and the galangin in the composition respectively are 30 μg/mL and 150 μg/mL.

Embodiment 3

A composition of hesperetin and galangin, where a mass ratio of the hesperetin and the galangin is 50:100, and specifically, concentrations of the hesperetin and the galangin in the composition respectively are 50 μg/mL and 100 μg/mL.

Embodiment 4

A composition of hesperetin and formononetin, where a mass ratio of the hesperetin and the formononetin is 30:20, and specifically, concentrations of the hesperetin and the formononetin in the composition respectively are 30 μg/mL and 20 μg/mL.

Embodiment 5

A composition of hesperetin and formononetin, where a mass ratio of the hesperetin and the formononetin is 30:30, and specifically, concentrations of the hesperetin and the formononetin in the composition respectively are 30 μg/mL and 30 μg/mL.

Embodiment 6

A composition of hesperetin and formononetin, where a mass ratio of the hesperetin and the formononetin is 50:20, and specifically, concentrations of the hesperetin and the formononetin in the composition respectively are 50 μg/mL and 20 μg/mL.

Hypoglycemic Effect Test of Hesperetin Composition

Experimental Method an α-glucosidase solution with a concentration being 0.25 U/mL and a substrate p-nitrophenyl-α-D-glucopyranoside (pNPG) solution with a concentration being 5 mmol/mL were prepared by using a PBS buffer solution (0.1 mol/L pH 6.8).

100 μL of sample solution was added to each hole, then 40 μL of α-glucosidase (0.25 U/mL) was added, reacted for 15 min at 37° C., and then 60 μL of substrate p-nitrophenyl-α-D-glucopyranoside (5 mmol/mL) was added; and after placed at 37° C. to react for 15 min, a microplate reader measured at a wave length of 405 nm.

The sample solution to be tested was the hesperetin composition described in Embodiments 1 to 6, and dimethyl sulfoxide (DMSO) was first used to prepare the hesperetin, galangin, and formononetin into mother liquor (10 mg/mL) respectively; and then the PBS buffer solution was used to prepare hesperetin, galangin, and formononetin with specific concentrations and the sample solution of the composition.

A positive control group was acarbose (350 μg/mL), a blank group was that samples and enzymes were not added, and a sample blank group was that enzymes were not added.

Calculation formula: inhibition rate=[1−(ODsample−ODsample blank)/(ODnegative control−ODblank)]×100%

CI values are calculated according to CompuSyn software to evaluate synergistic effect among drugs.

Combination Index (CI) is used to describe the strength of the synergistic effect of the drugs; CI<1 represents that the synergistic effect exists among drugs, combination can strengthen the therapeutic effect of various monomer drugs, and the smaller the CI values, the stronger the synergistic effect; CI=1 represents that adduction exists among drugs, and a combination result is just linear superposition of the therapeutic effect of various monomer drugs; and CI>1 represents that an antagonistic effect exists among drugs, and combination may reduce the therapeutic effect of each monomer drug inversely.

1. The Inhibitory Activity of Hesperetin Composition in Embodiment 1 and Embodiment 4 on α-Glucosidase The inhibitory activity of the hesperetin composition in Embodiment 1 and Embodiment 4 on the α-glucosidase is as shown in FIG. 1: inhibition rates of hesperetin (30 μg/mL), galangin (100 μg/mL), formononetin (20 μg/mL), and acarbose (350 μg/mL) at corresponding mass concentrations respectively are 45.2±3.2%, 56.32±4.5%, 60.07±5.3%, and 46.25±3.5%; the inhibition rate of the composition of the hesperetin and the galangin (30+100 μg/mL) is 92.8±6.4%, and the inhibition rate of the hesperetin and the formononetin (30+20 μg/mL) is 77.31±4.5%; and the result shows that the composition significantly improves the inhibitory activity on the α-glucosidase during combination.

Figure 2:
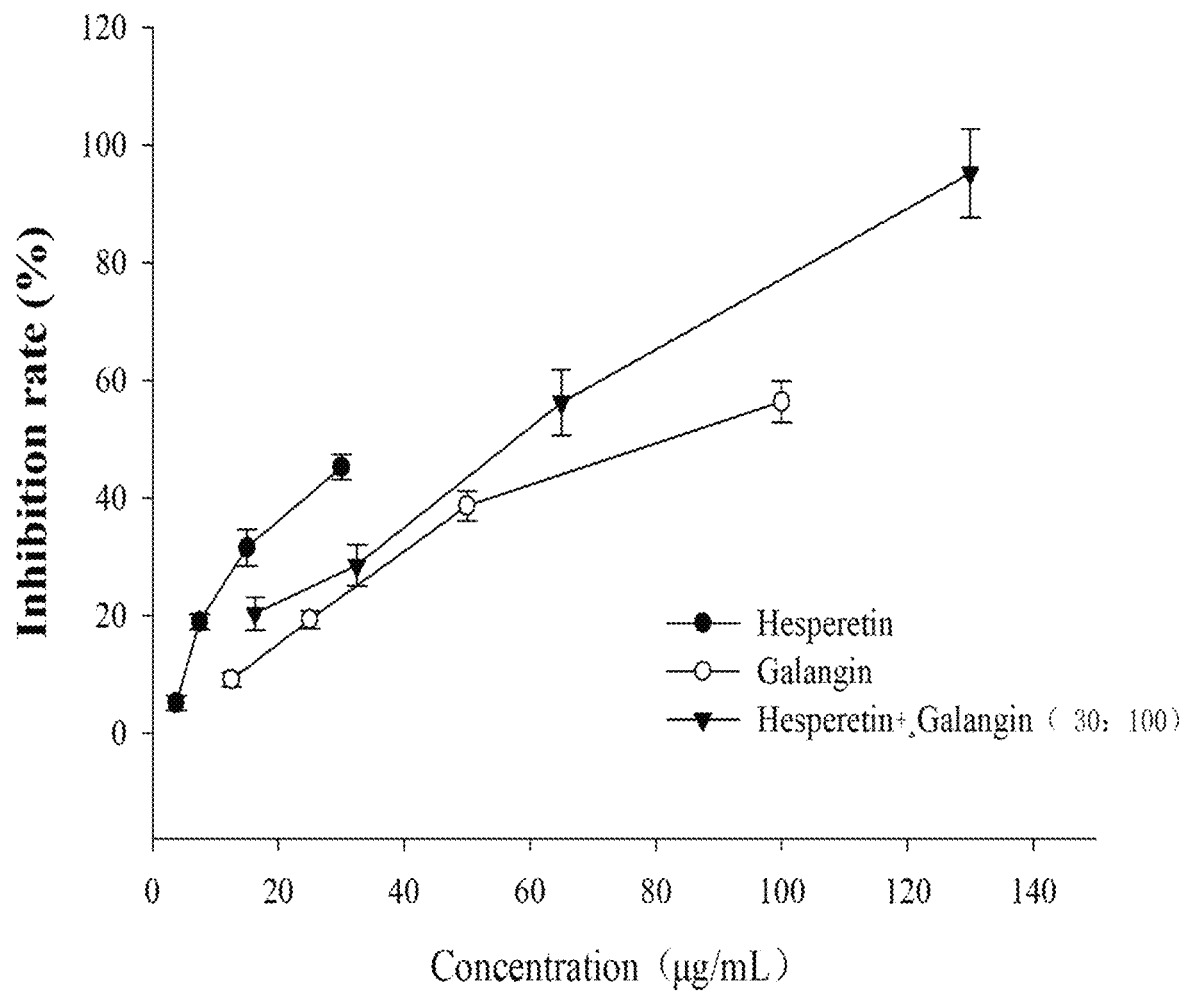
FIG. 2 is an inhibition curve diagram of a composition of hesperetin and galangin (30:100) on α-glucosidase.
Figure 3:
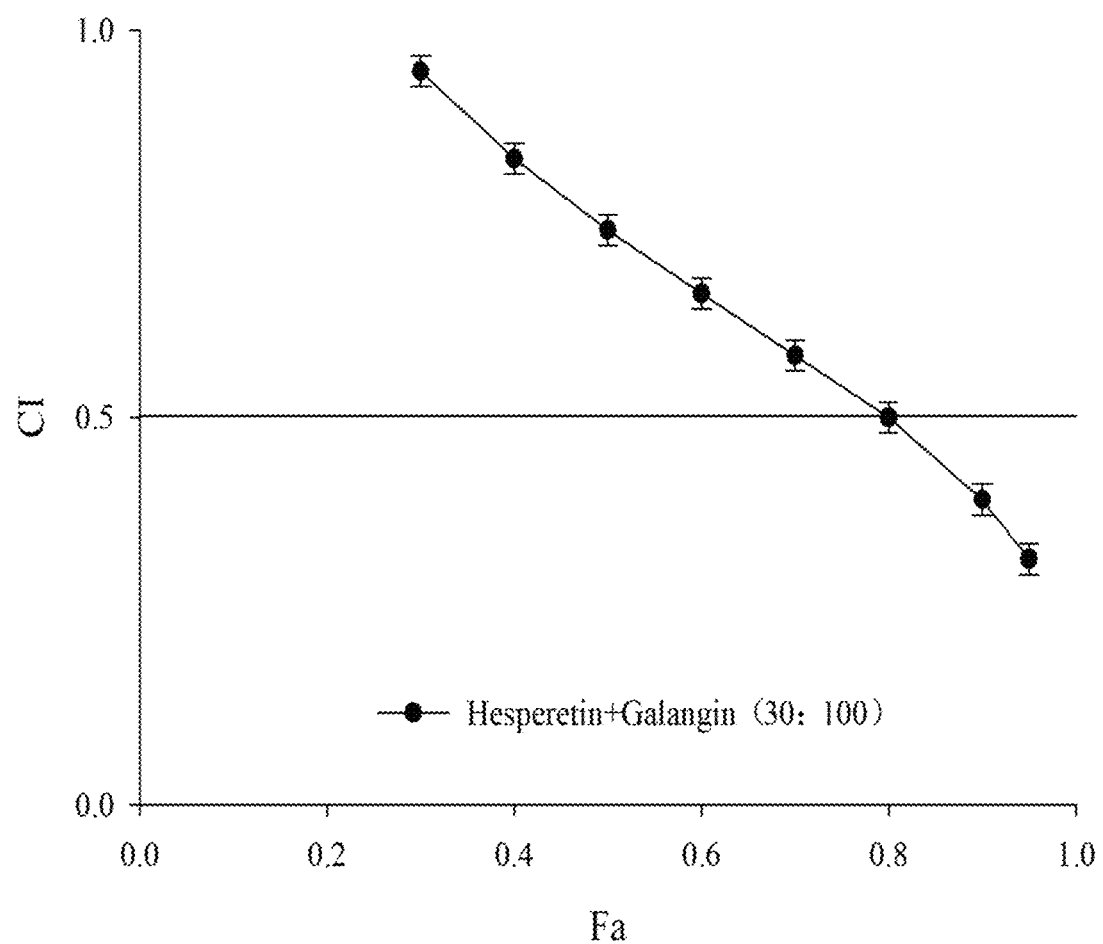
FIG. 3 is an Fa-CI trend graph of a composition of hesperetin and galangin (30:100) on α-glucosidase.

The inhibitory activity of the composition of the hesperetin and the galangin with a mass ratio being 30:100 on the α-glucosidase under different concentration gradients is tested, and the concentration gradients of the composition of the hesperetin and the galangin are (m/mL): 30+100, 15+50, 7.5+25, and 3.75+12.5; the concentration gradients of the hesperetin are (m/mL): 30, 15, 7.5, and 3.75; the concentration gradients of the galangin are (m/mL): 100, 50, 25, and 12.5; the result is shown in FIG. 2; and the composition of the hesperetin and the galangin with a mass ratio being 30:100 improves the inhibitory activity on the α-glucosidase under different concentration gradients. An Fa-CI trend graph of the composition of the hesperetin and the galangin with a mass ratio being 30:100 is as shown in FIG. 3, and as can be known from FIG. 3, CI values of the hesperetin and the galangin are below 1.0, which shows a synergistic effect.

Figure 4:
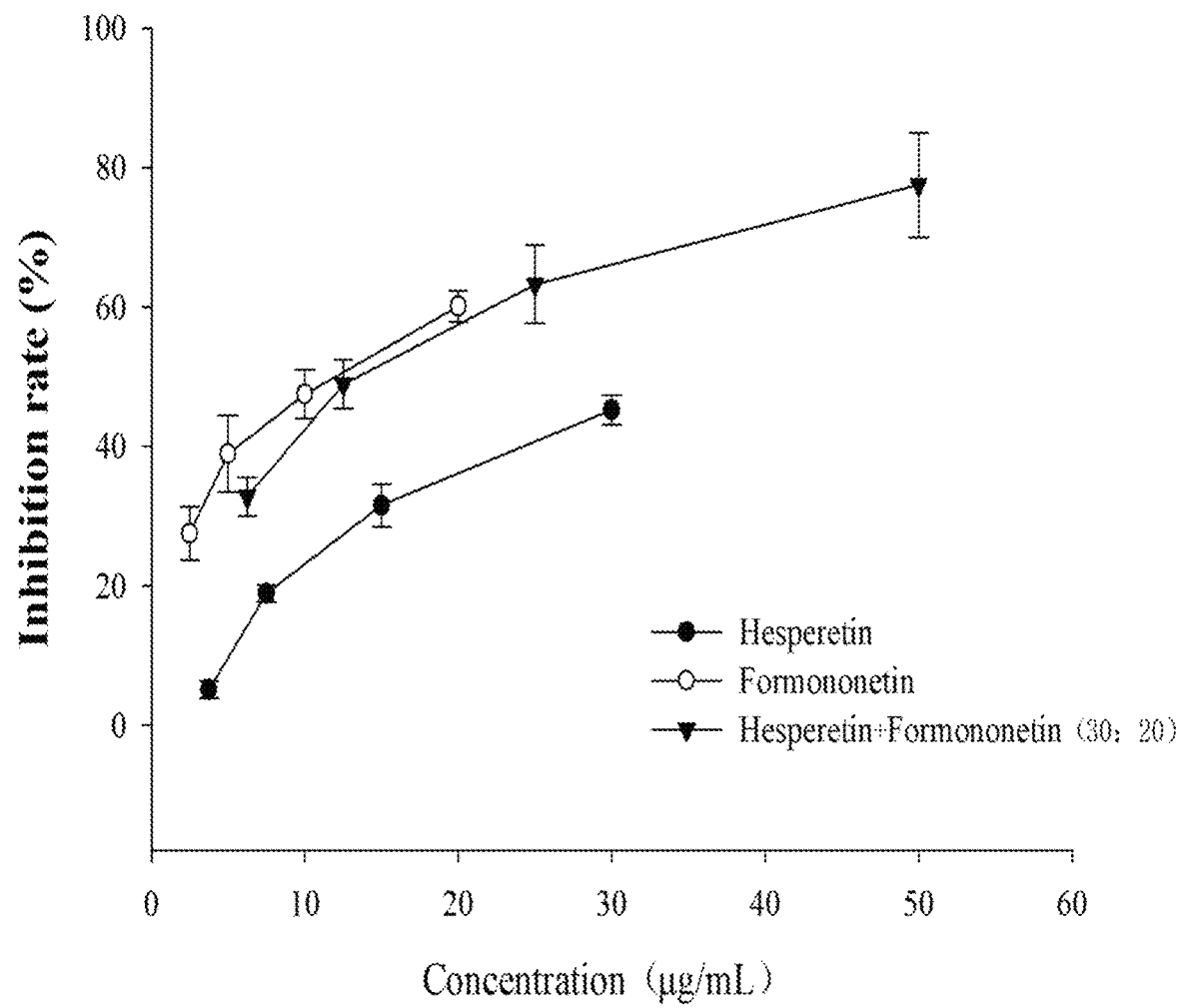
FIG. 4 is an inhibition curve diagram of a composition of hesperetin and formononetin (30:20) on α-glucosidase.
Figure 5:
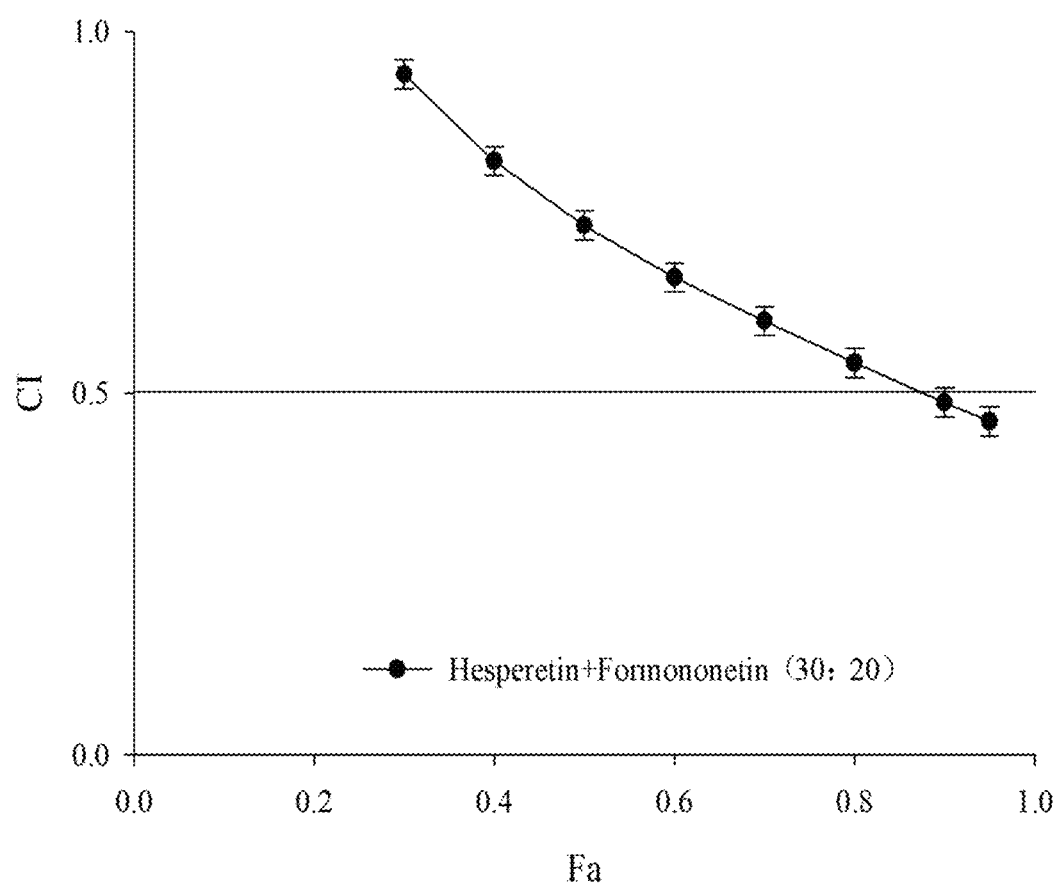
FIG. 5 is an Fa-CI trend graph of a composition of hesperetin and formononetin (30:20) on α-glucosidase.

The inhibitory activity of the composition of the hesperetin and the formononetin with a mass ratio being 30:20 on the α-glucosidase under different concentration gradients is tested, and the concentration gradients of the composition of the hesperetin and the formononetin are (m/mL): 30+20, 15+10, 7.5+5, and 3.75+2.5; the concentration gradients of the hesperetin are (m/mL): 30, 15, 7.5, and 3.75; the concentration gradients of the formononetin are (m/mL): 20, 10, 5, and 2.5; the result is shown in FIG. 4; and the composition of the hesperetin and the formononetin with a mass ratio being 30:20 also correspondingly improves the inhibitory activity on the α-glucosidase under different concentration gradients. An Fa-CI trend graph of the composition of the hesperetin and the formononetin with a mass ratio being 30:20 is as shown in FIG. 5, and as can be known from FIG. 5, CI values of the hesperetin and the formononetin are below 1.0, which shows a synergistic effect.

CI of the hesperetin composition in Embodiment 1 and Embodiment 4 is as shown in Table 1:

TABLE 1

| | | CI of a Hesperetin Composition in Embodiment 1 and Embodiment 4 | | | |
|---|---|---|---|---|---|
| Compound | Mass ratio | CI | | | |
| | | $GI_{50}$ | $GI_{75}$ | $GI_{90}$ | $CI_{avg}$ |
| Hesperetin + Galangin | 30:100 | 0.72 ± 0.01 | 0.51 ± 0.02 | 0.37 ± 0.01 | 0.48 |

TABLE 1-continued

CI of a Hesperetin Composition in Embodiment 1 and Embodiment 4

| Compound | Mass ratio | CI | | | |
|---|---|---|---|---|---|
| | | $GI_{50}$ | $GI_{75}$ | $GI_{90}$ | $CI_{avg}$ |
| Hesperetin + Formononetin | 30:20 | 0.73 ± 0.02 | 0.57 ± 0.03 | 0.49 ± 0.02 | 0.56 |

Data comes from results of three independent experiments and is represented as average value±standard difference As can be known from the result of Table 1 that CIs during combination of the hesperetin and the galangin (30:100) and combination of the hesperetin and the formononetin (30:20) are less than 1, which shows a synergistic effect, where the CI of the composition of the hesperetin and the galangin is within GI75 and GI90 and is less than 0.60, which shows a strong synergistic effect, and an average value of the CI ($CI_{avg}$) is 0.48; and the CI of the composition of the hesperetin and to formononetin is within $GI_{75}$ and $GI_{90}$ and is less than 0.6, which also shows a strong synergistic effect, and an average value of the CI ($CI_{avg}$) is 0.56.

Figure 6:
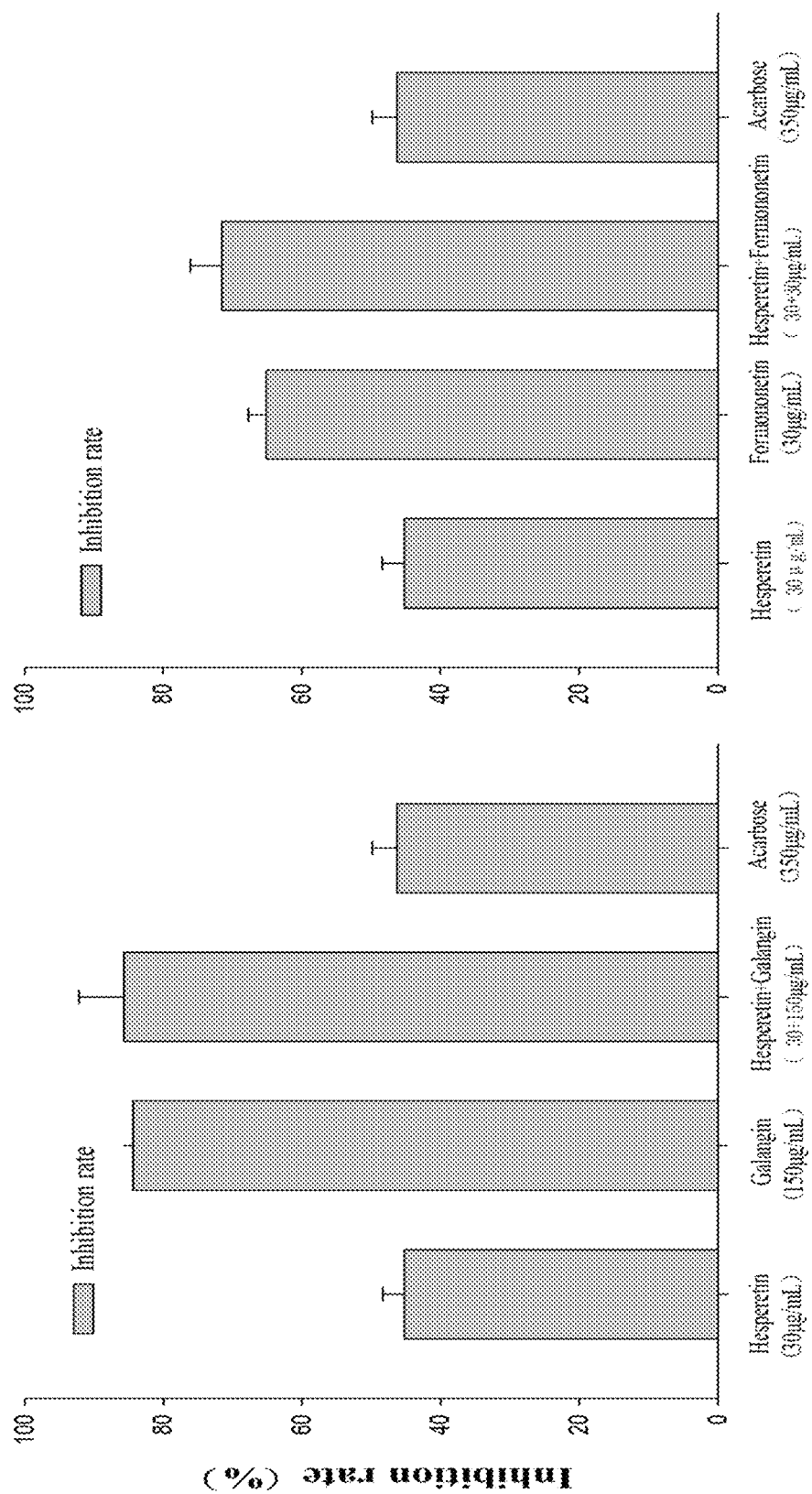
FIG. 6 shows inhibitory activity of a hesperetin composition in Embodiment 2 and Embodiment 5 on α-glucosidase.

2. The Inhibitory Activity of Hesperetin Composition in Embodiment 2 and Embodiment 5 on α-Glucosidase The inhibitory activity of the hesperetin composition in Embodiment 2 and Embodiment 5 on the α-glucosidase is as shown in FIG. 6: inhibition rates of hesperetin (30 μg/mL), galangin (150 μg/mL), formononetin (30 μg/mL), and acarbose (350 μg/mL) at corresponding mass concentrations respectively are 45.2±3.2%, 84.4±7.5%, 65.2±4.3%, and 46.25±3.5%; the inhibition rate of the composition of the hesperetin and the galangin (30+150 μg/mL) is 85.7±6.7%, and the inhibition rate of the hesperetin and the formononetin (30+30 μg/mL) is 71.6±3.5%; and the result shows that the composition does not significantly improve the inhibitory activity on the α-glucosidase during combination.

Figure 7:
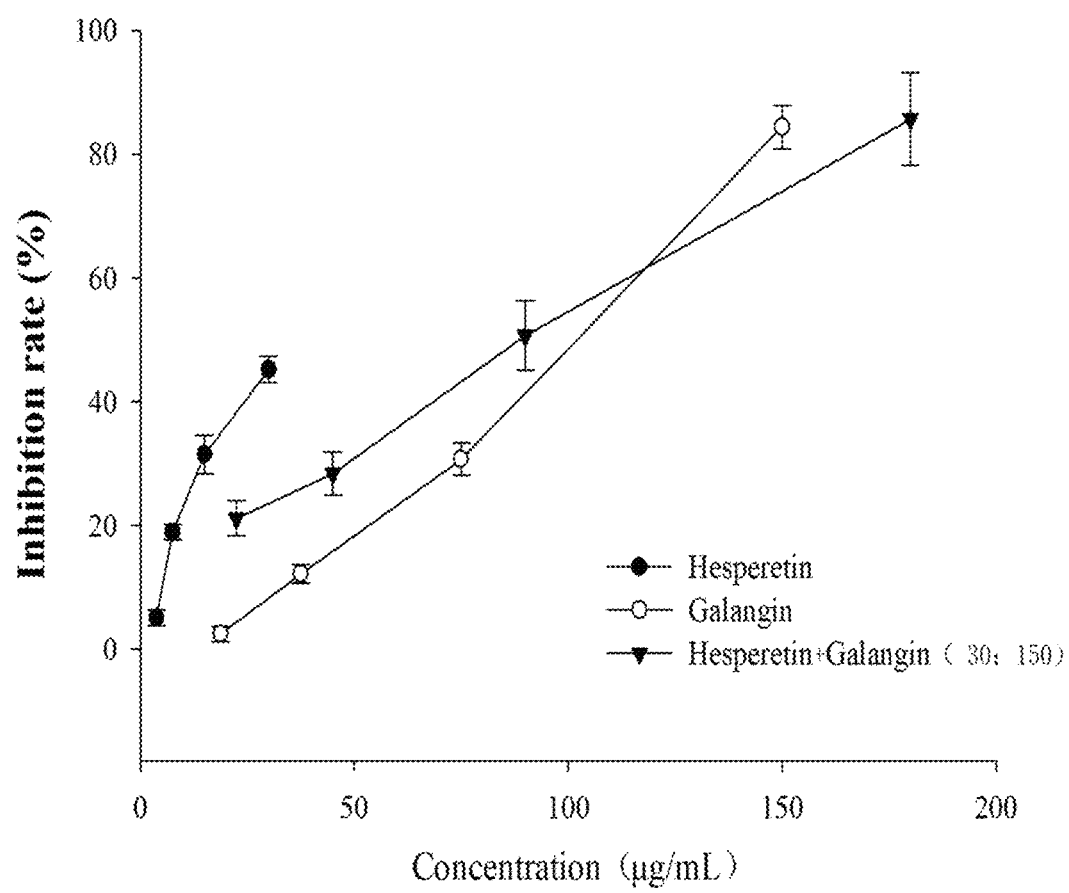
FIG. 7 is an inhibition curve diagram of a composition of hesperetin and galangin (30:150) on α-glucosidase.

The inhibitory activity of the composition of the hesperetin and the galangin with a mass ratio being 30:150 on the α-glucosidase under different concentration gradients is tested, and the concentration gradients of the composition of the hesperetin and the galangin are (μg/mL): 30+150, 15+75, 7.5+37.5, and 3.75+18.75; the concentration gradients of the hesperetin are (μg/mL): 30, 15, 7.5, and 3.75; the concentration gradients of the galangin are (μg/mL): 150, 75, 37.5, and 18.75; and the result is shown in FIG. 7.

Figure 8:
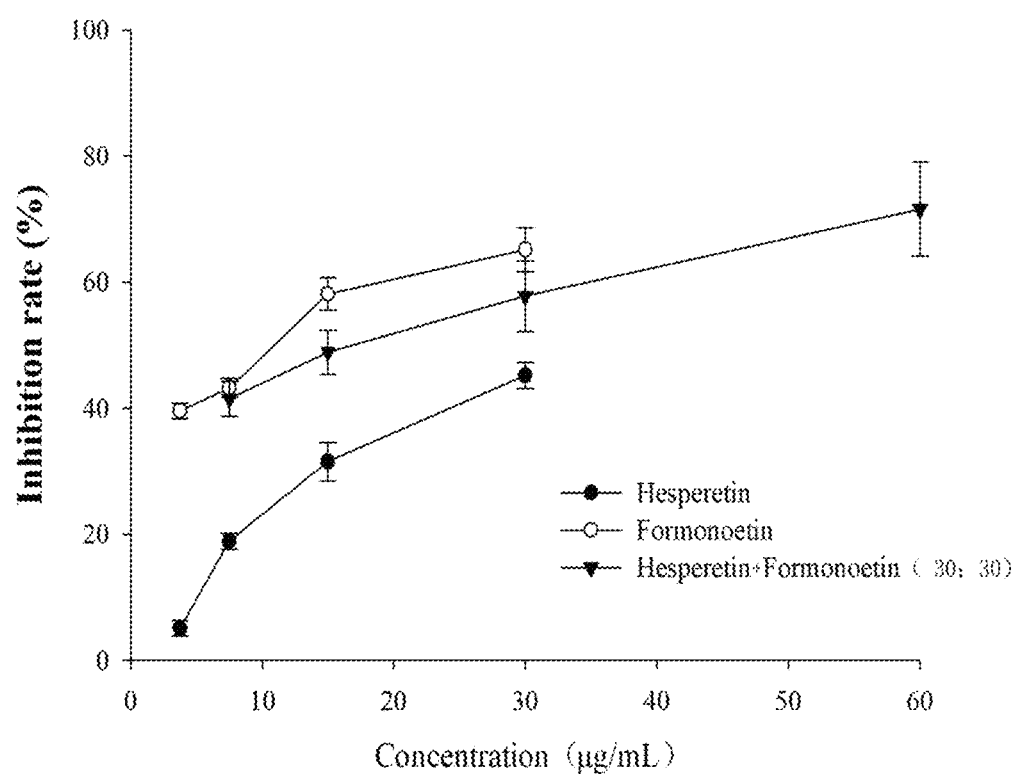
FIG. 8 is an inhibition curve diagram of a composition of hesperetin and formononetin (30:30) on α-glucosidase.

The inhibitory activity of the composition of the hesperetin and the formononetin with a mass ratio being 30:30 on the α-glucosidase under different concentration gradients is tested, and the concentration gradients of the composition of the hesperetin and the formononetin are (μg/mL): 30+30, 15+15, 7.5+7.5, and 3.75+3.75; the concentration gradients of the hesperetin are (μg/mL): 30, 15, 7.5, and 3.75; the concentration gradients of the formononetin are (μg/mL): 30, 15, 7.5, and 3.75; and the result is shown in FIG. 8.

CI of the hesperetin composition in Embodiment 2 and Embodiment 5 is as shown in Table 2:

TABLE 2

CI of a Hesperetin Composition in Embodiment 2 and Embodiment 5

| Compound | Mass ratio | CI | | | |
|---|---|---|---|---|---|
| | | $GI_{50}$ | $GI_{75}$ | $GI_{90}$ | $CI_{avg}$ |
| Hesperetin + Galangin | 30:150 | >1 | >1 | >1 | >1 |
| Hesperetin + Formononetin | 30:30 | >1 | >1 | >1 | >1 |

Data comes from results of three independent experiments and is represented as average value±standard difference As can be known from the result of Table 2 that CIs during combination of the hesperetin and the galangin (30:150) and combination of the hesperetin and the formononetin (30:30) are greater than 1, which shows an antagonistic effect.

Figure 9:
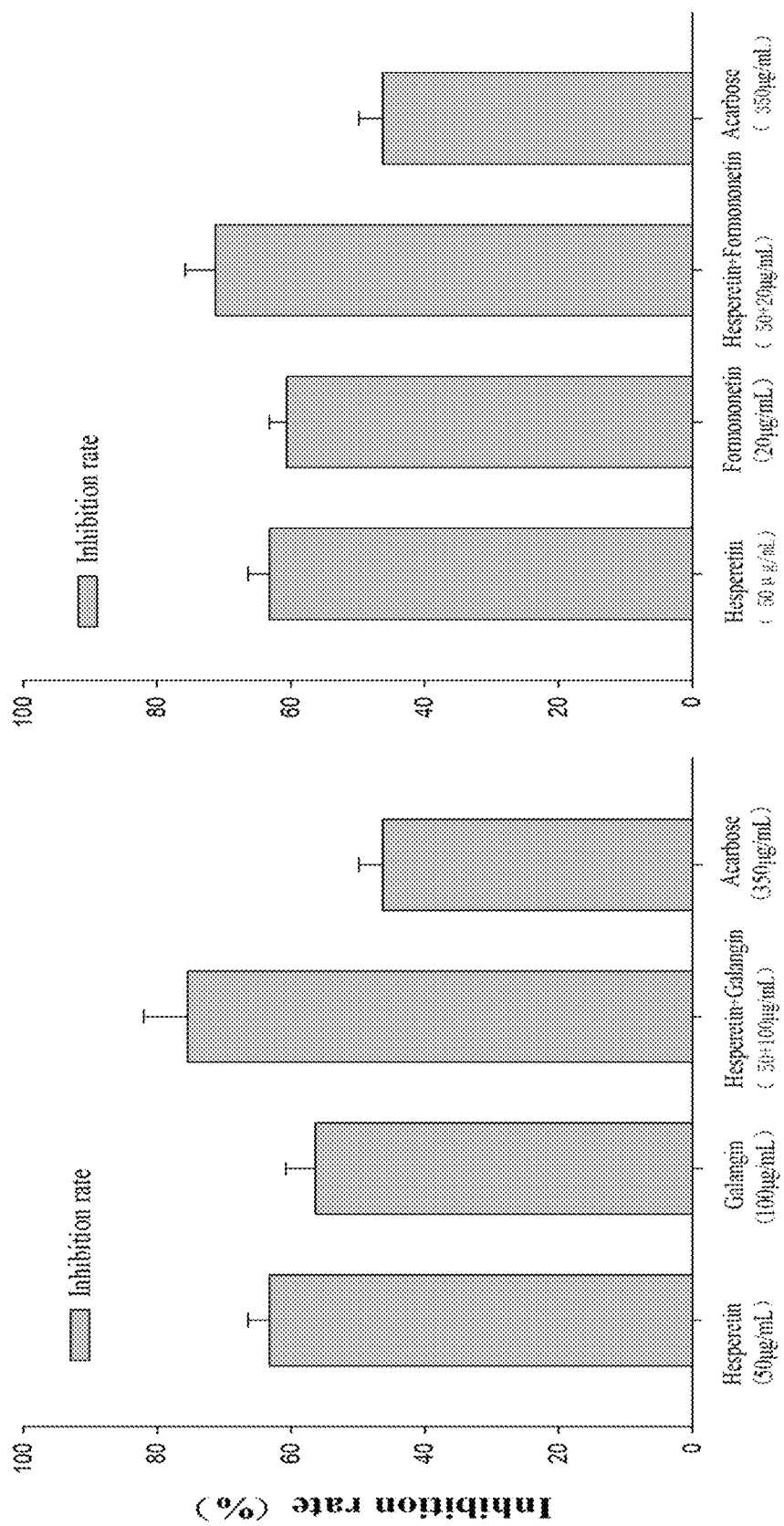
FIG. 9 shows inhibitory activity of a hesperetin composition in Embodiment 3 and Embodiment 6 on α-glucosidase.

3. The Inhibitory Activity of Hesperetin Composition in Embodiment 3 and Embodiment 6 on α-Glucosidase The inhibitory activity of the hesperetin composition in Embodiment 3 and Embodiment 6 on the α-glucosidase is as shown in FIG. 9: inhibition rates of hesperetin (50 μg/mL), galangin (+100 μg/mL), formononetin (20 μg/mL), and acarbose (350 μg/mL) at corresponding mass concentrations respectively are 63.4±4.2%, 56.32±4.5%, 60.07±5.3%, and 46.25±3.5%; the inhibition rate of the composition of the hesperetin and the galangin (50+100 μg/mL) is 75.5±5.3%, and the inhibition rate of the hesperetin and the formononetin (50+20 μg/mL) is 71.31±3.5%; and the result shows that the composition does not significantly improve the inhibitory activity on the α-glucosidase during combination.

Figure 10:
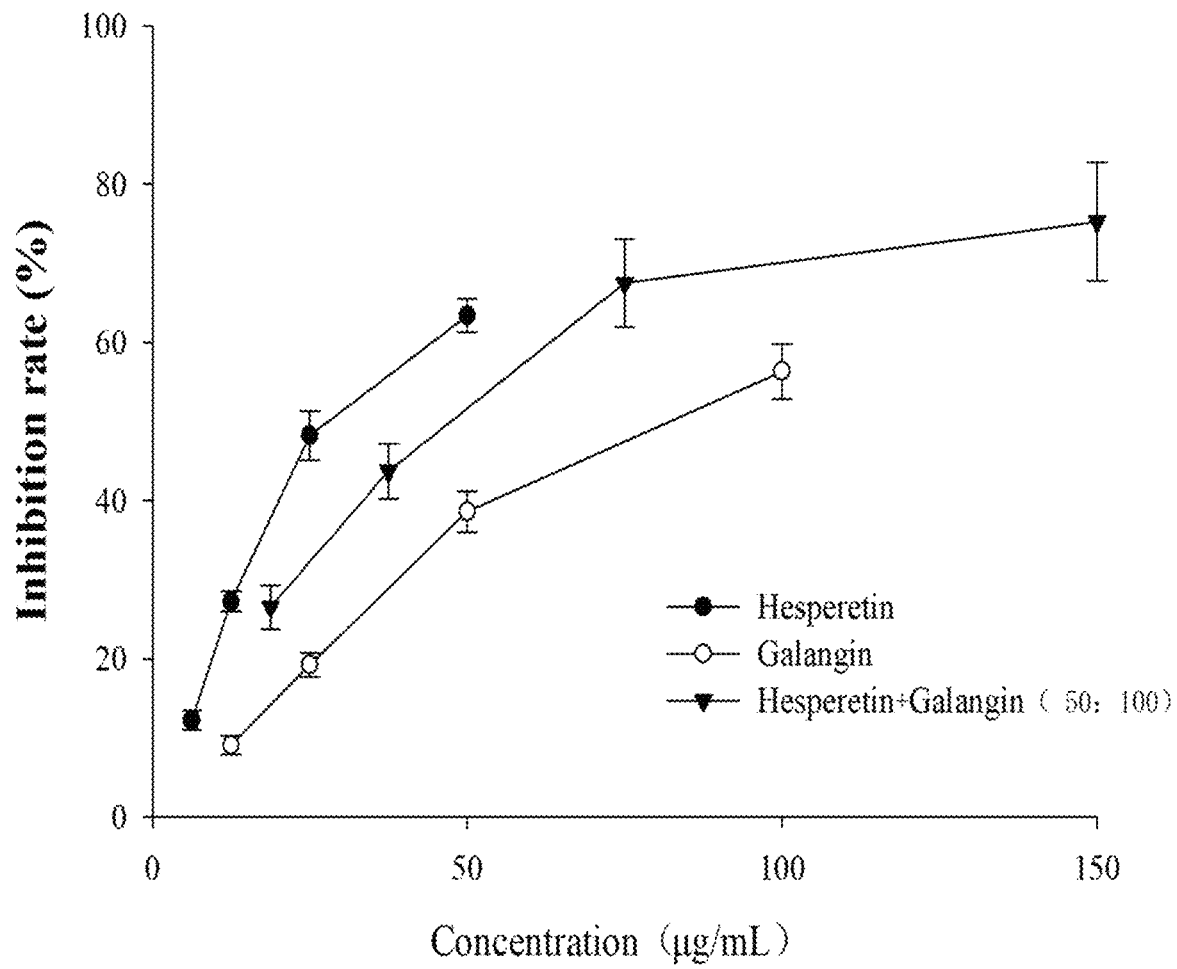
FIG. 10 is an inhibition curve diagram of a composition of hesperetin and galangin (50:100) on α-glucosidase.

The inhibitory activity of the composition of the hesperetin and the galangin with a mass ratio being 50:100 on the α-glucosidase under different concentration gradients is tested, and the concentration gradients of the composition of the hesperetin and the galangin are (μ/mL): 50+100, 25+50, 12.5+25, and 6.25+12.5; the concentration gradients of the hesperetin are (μg/mL): 50, 25, 12.5, and 6.25; the concentration gradients of the galangin are (μg/mL): 100, 50, 25, and 12.5; and the result is shown in FIG. 10.

Figure 11:
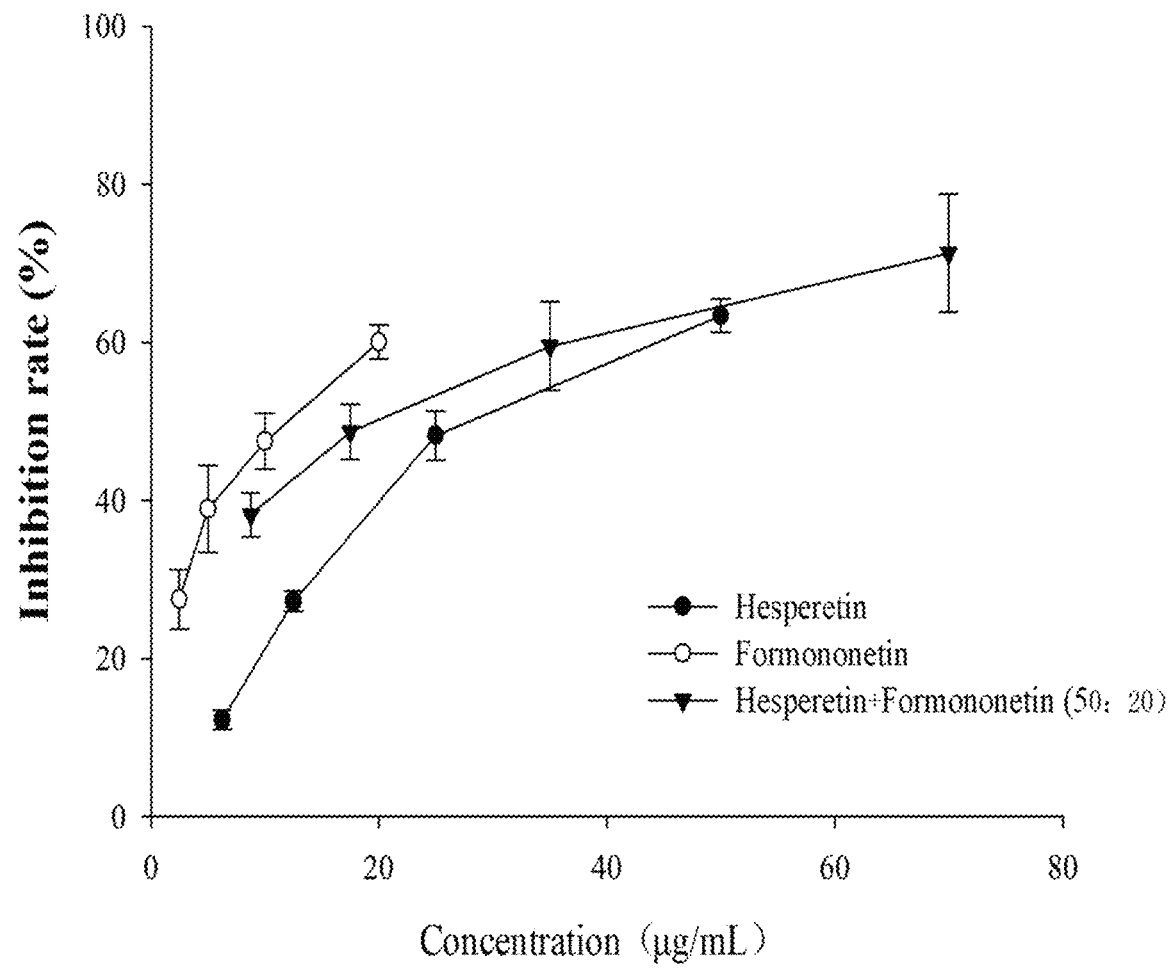
FIG. 11 is an inhibition curve diagram of a composition of hesperetin and formononetin (50:20) on α-glucosidase.

The inhibitory activity of the composition of the hesperetin and the formononetin with a mass ratio being 50:20 on the α-glucosidase under different concentration gradients is tested, and the concentration gradients of the composition of the hesperetin and the formononetin are (μg/mL): 50+20, 25+10, 12.5+5, and 6.25+2.5; the concentration gradients of the hesperetin are (μg/mL): 50, 25, 12.5, and 6.25; the concentration gradients of the formononetin are (μg/mL): 20, 10, 5, and 2.5; and the result is shown in FIG. 11.

CI of the hesperetin composition in Embodiment 3 and Embodiment 6 is as shown in Table 3:

TABLE 3

CI of a Hesperetin Composition in
Embodiment 3 and Embodiment 6

| Compound | Mass ratio | CI | | | |
|---|---|---|---|---|---|
| | | $GI_{50}$ | $GI_{75}$ | $GI_{90}$ | $CI_{avg}$ |
| Hesperetin + Galangin | 50:100 | >1 | >1 | >1 | >1 |
| Hesperetin + Formononetin | 50:20 | >1 | >1 | >1 | >1 |

Data comes from results of three independent experiments and is represented as average value±standard difference As can be known from the result of Table 3 that CIs during combination of the hesperetin and the galangin (50:100) and combination of the hesperetin and the formononetin (50:20) are greater than 1, which shows an antagonistic effect.

Comparative Example 1

Genistein is similar to formononetin in structure, and a molecular formula thereof is $C_{15}H_{10}O_5$; a molecular weight is: 270.24; a CAS accession number is: 446-72-0; and a structural formula is:

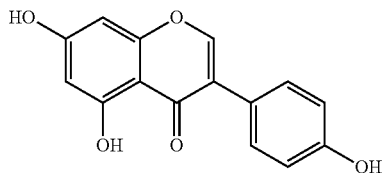 [SMILES: O=c1c(-c2ccc(O)cc2)coc2cc(O)cc(O)c12]

A composition of hesperetin and genistein, where a mass ratio of the hesperetin and the genistein is 30:2, and specifically, concentrations of the hesperetin and the genistein respectively are 30 μg/mL and 2 μg/mL.

Figure 12:
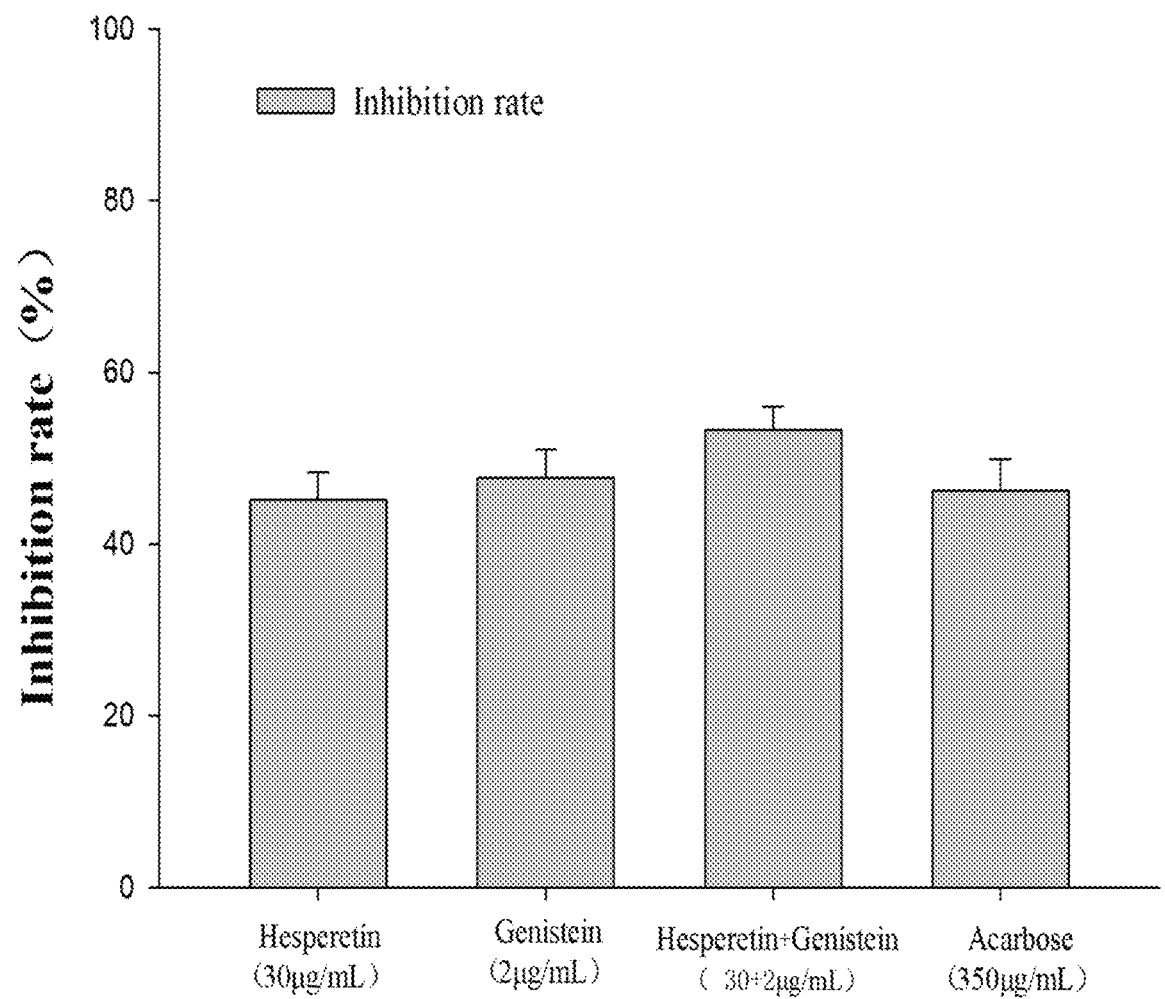
FIG. 12 shows that a hesperetin composition of Embodiment 1 inhibits activity of α-glucosidase.

Testing the inhibitory activity of the composition of the hesperetin and the genistein in Comparative example 1 on the α-glucosidase is as shown in FIG. 12: inhibition rates, on the α-glucosidase, of hesperetin (30 μg/mL), genistein (2 μg/mL), and acarbose (350 μg/mL) at corresponding mass concentrations respectively are 45.2±3.2%, 47.7±3.3%, and 46.25±3.5%; the inhibition rate of the composition of the hesperetin and the genistein (30+2 μg/mL) is 53.3±2.7%; and the result shows that the composition slightly improves the inhibitory activity of the α-glucosidase during combination.

Figure 13:
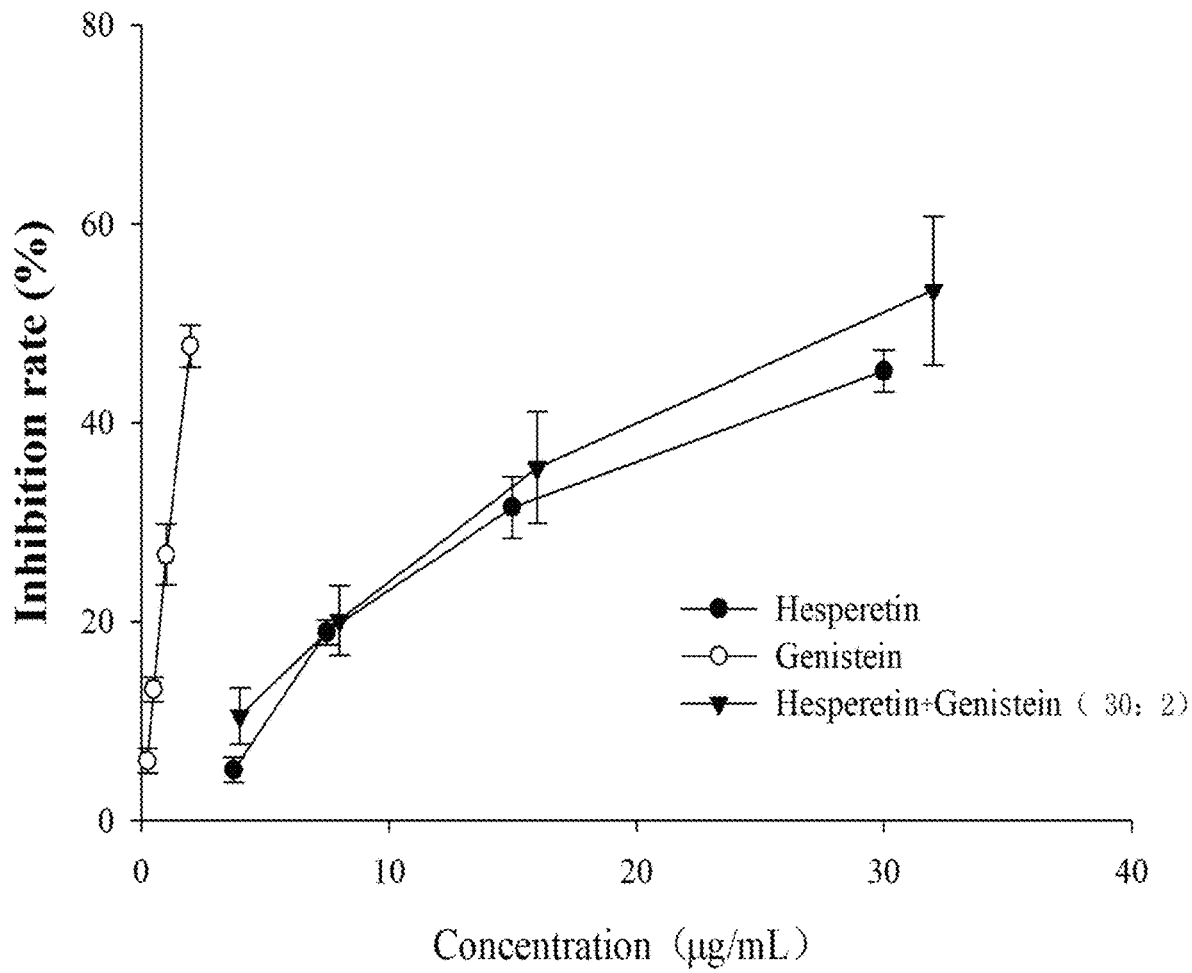
FIG. 13 is an inhibition curve diagram of a composition of hesperetin and genistein (30:2) on α-glucosidase.

The inhibitory activity of the composition of the hesperetin and the genistein with a mass ratio being 30:2 on the α-glucosidase under different concentration gradients is tested, and the concentration gradients of the composition of the hesperetin and the genistein are (μg/mL): 30+2, 15+1, 7.5+0.5, and 3.75+0.25; the concentration gradients of the hesperetin are (μg/mL): 30, 15, 7.5, and 3.75; the concentration gradients of the genistein are (μg/mL): 2, 1, 0.5, and 0.25; and the result is shown in FIG. 13.

CI of the hesperetin composition in Comparative example 1 is as shown in Table 4:

TABLE 4

CI of a Hesperetin Composition in Comparative example 1

| Compound | Mass ratio | CI | | | |
|---|---|---|---|---|---|
| | | $GI_{50}$ | $GI_{75}$ | $GI_{90}$ | $CI_{avg}$ |
| Hesperetin + Genistein | 30:2 | >1 | >1 | >1 | >1 |

Data comes from results of three independent experiments and is represented as average value±standard difference As can be known from the result of Table 4 that although the inhibitory activity on the α-glucosidase is improved when the composition of the hesperetin and the genistein (30:2) is combined, the CI during combination of the hesperetin and the genistein (30:2) is greater than 1, which shows an antagonistic effect.

Comparative Example 2

This embodiment shows that the combination of various monomer compounds and hesperetin does not have the synergistic effect. Various monomer compounds are selected from morin, luteolin, myricetin, herbacetin, dihydromorin, naringenin, fisetin, baicalein, apigenin, kaempferide, cyanidin, chrysin, genkwanin, vitexin, phloretin, biochanin A, and calycosin.

First, the inhibition rates of various monomer compounds under corresponding concentrations on the α-glucosidase are tested according to the above method, as shown in the following Table 5:

TABLE 5

| Monomer compound | Mass concentration (μg/mL) | Inhibition rate |
|---|---|---|
| Hesperetin | 30 | 45.2 ± 3.2% |
| Morin | 1 | 41.2 ± 2.7% |
| Luteolin | 1 | 45.5 ± 2.7% |
| Myricetin | 1 | 41.2 ± 1.5% |
| Herbacetin | 2.5 | 35.2 ± 1.2% |
| Dihydromorin | 15 | 25.7 ± 4.7% |
| Naringenin | 25 | 50.5 ± 4.3% |
| Fisetin | 6 | 46.5 ± 2.3% |
| Baicalein | 10 | 38.8 ± 3.3% |
| Apigenin | 6 | 56.1 ± 4.4% |
| Kaempferide | 5 | 30.8 ± 1.3% |
| Cyanidin | 0.7 | 47.5 ± 1.4% |
| Chrysin | 100 | 51.2 ± 5.5% |
| Genkwanin | 35 | 70.12 ± 5.5% |
| Vitexin | 10 | 29.2 ± 1.4% |
| Phloretin | 8 | 46.3 ± 2.7% |
| Biochanin A | 0.7 | 38.5 ± 2.1% |
| Calycosin | 6 | 56.6 ± 4.3% |

Then, various monomer compounds and hesperetin are combined to test the inhibition rate of the composition on the α-glucosidase, as shown in the following Table 6:

TABLE 6

| Monomer compound | Monomer compound | Mass concentration ratio | Inhibition rate |
|---|---|---|---|
| Hesperetin | Morin | 30:1 | 32.3 ± 1.1% |
| | Luteolin | 30:1 | 26.8 ± 0.8% |
| | Myricetin | 30:1 | 15.3 ± 1.1% |
| | Herbacetin | 30:2.5 | 25.3 ± 1.7% |
| | Dihydromorin | 30:15 | 25.3 ± 1.2% |

TABLE 6-continued
| Monomer compound | Monomer compound | Mass concentration ratio | Inhibition rate |
|---|---|---|---|
| | 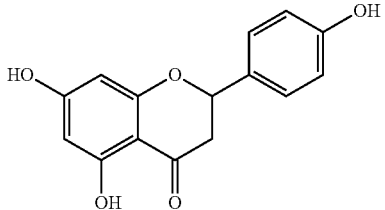<br>Naringenin | 30:25 | 43.3 ± 2.7% |
| | 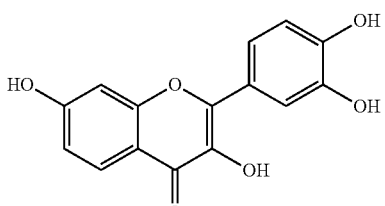<br>Fisetin | 30:6 | 26.5 ± 1.8% |
| | 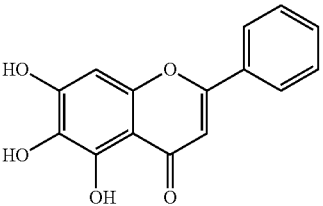<br>Baicalein | 30:10 | 29.3 ± 1.6% |
| | 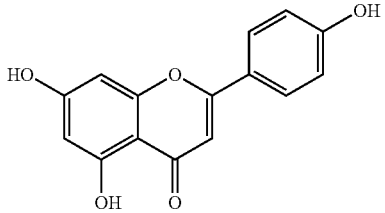<br>Apigenin | 30:6 | 25.3 ± 0.8% |
| | 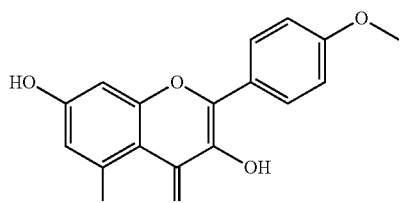<br>Kaempferide | 30:5 | 32.3 ± 2.2% |

TABLE 6-continued
| Monomer compound | Monomer compound | Mass concentration ratio | Inhibition rate |
|---|---|---|---|
| | 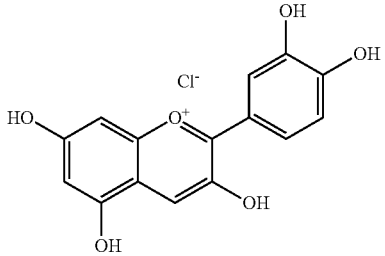<br>Cyanidin | 30:0.7 | 23.1 ± 0.7% |
| | 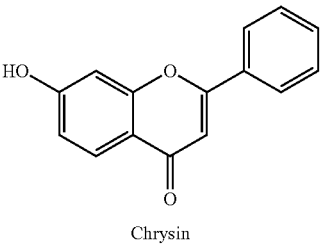 [SMILES: O=c1cc(-c2ccccc2)oc2cc(O)ccc12]<br>Chrysin | 30:100 | 36.7 ± 1.5% |
| | 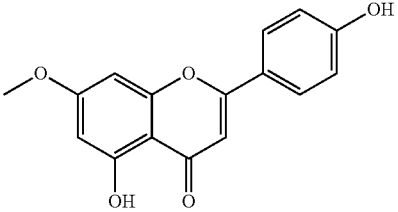<br>Genkwanin | 30:35 | 53.3 ± 2.8% |
| | 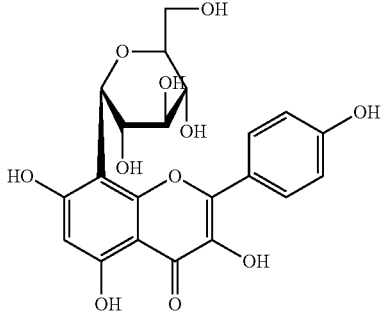<br>Vitexin | 30:10 | 20.3 ± 0.3% |
| | 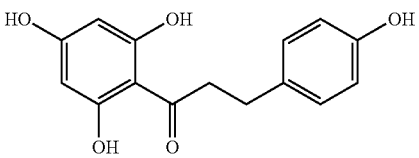<br>Phloretin | 30:8 | 48.3 ± 3.4% |

TABLE 6-continued

| Monomer compound | Monomer compound | Mass concentration ratio | Inhibition rate |
|---|---|---|---|
| | 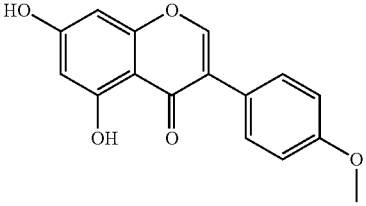  Biochanin A | 30:0.7 | 34.5 ± 2.3% |
| | 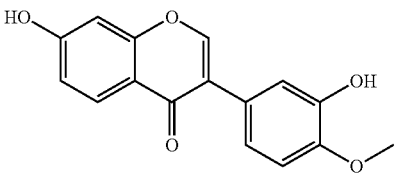  Calycosin | 30:6 | 31.3 ± 2.5% |

As can be seen from Table 6 that after various monomer compounds are combined with the hesperetin, the inhibition rate of the composition is directly lower than the inhibition rate of a single compound, and the composition shows an antagonistic effect actually without the synergistic effect.

Comparative Example 3

This embodiment shows that the combination of various monomer compounds and galangin does not have the synergistic effect. Various monomer compounds are selected from morin, vitexin, kaempferide, apigenin, kaempferol, dihydromorin, fisetin, naringenin, myricetin, luteolin, daidzein, biochanin A, phloretin, isoliquiritigenin, cyanidin, and delphinidin.

First, the inhibition rates of various monomer compounds under corresponding concentrations on the α-glucosidase are tested according to the above method, as shown in the following Table 7:

TABLE 7

| Monomer compound | Mass concentration (μg/mL) | Inhibition rate |
|---|---|---|
| Galangin | 100 | 56.32 ± 4.5% |
| Morin | 1 | 41.2 ± 2.7% |

TABLE 7-continued

| Monomer compound | Mass concentration (μg/mL) | Inhibition rate |
|---|---|---|
| Vitexin | 10 | 29.2 ± 1.4% |
| Kaempferide | 5 | 30.8 ± 1.3% |
| Apigenin | 6 | 56.1 ± 4.4% |
| Kaempferol | 2.5 | 40.83 ± 2.3% |
| Dihydromorin | 15 | 25.7 ± 4.7% |
| Fisetin | 6 | 46.5 ± 2.3% |
| Naringenin | 25 | 50.5 ± 4.3% |
| Myricetin | 1 | 41.2 ± 1.5% |
| Luteolin | 1 | 45.5 ± 2.7% |
| Daidzein | 8 | 44.5 ± 2.5% |
| Biochanin A | 0.7 | 38.5 ± 2.1% |
| Phloretin | 8 | 46.3 ± 2.7% |
| Isoliquiritigenin | 4 | 35.2 ± 2.5% |
| Cyanidin | 0.7 | 47.5 ± 1.4% |
| Delphinidin | 1 | 50.2 ± 4.3% |

Then, various monomer compounds and galangin are combined to test the inhibition rate of the composition on the α-glucosidase, as shown in the following Table 8:

TABLE 8

| Monomer compound | Monomer compound | Mass concentration ratio | Inhibition rate |
|---|---|---|---|
| 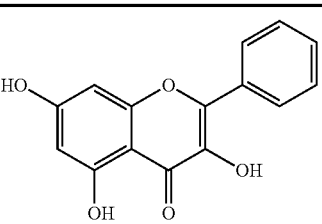  Galangin | 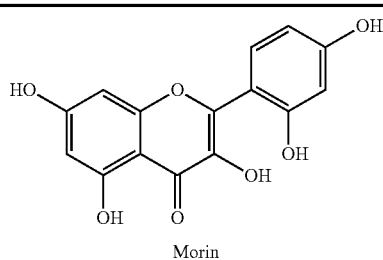  Morin | 100:1 | 36.7 ± 1.2% |

TABLE 8-continued

| Monomer compound | Monomer compound | Mass concentration ratio | Inhibition rate |
|---|---|---|---|
| | Vitexin | 100:10 | 24.7 ± 1.3% |
| | Kaempferide | 100:5 | 52.1 ± 1.5% |
| | Apigenin | 100:6 | 44.3 ± 2.1% |
| | Kaempferol | 100:2.5 | 44.3 ± 2.3% |
| | Dihydromorin | 100:15 | 23.7 ± 0.8% |
| | Fisetin | 100:6 | 16.3 ± 0.5% |

TABLE 8-continued

| Monomer compound | Monomer compound | Mass concentration ratio | Inhibition rate |
|---|---|---|---|
| | Naringenin | 100:25 | 43.7 ± 3.1% |
| | Myricetin | 100:1 | 16.9 ± 0.5% |
| | Luteolin | 100:1 | 34.1 ± 1.8% |
| | Daidzein | 100:8 | 27.6 ± 1.5% |
| | Biochanin A | 100:0.7 | 22.3 ± 1.7% |
| | Phloretin | 100:8 | 51.3 ± 1.7% |

TABLE 8-continued

| Monomer compound | Monomer compound | Mass concentration ratio | Inhibition rate |
|---|---|---|---|
| | 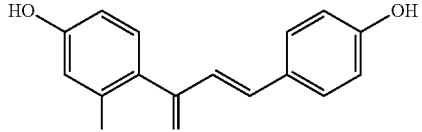<br>Isoliquiritigenin | 100:4 | 53.1 ± 2.8% |
| | 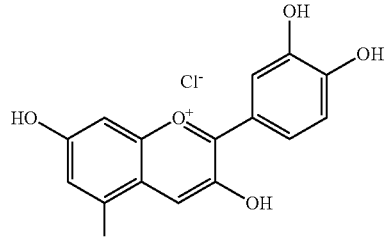<br>Cyanidin | 100:0.7 | 48.3 ± 2.7% |
| | 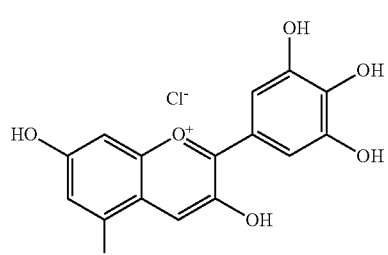<br>Delphinidin | 100:1 | 49.3 ± 1.8% |

As can be seen from Table 8 that after various monomer compounds are combined with the galangin, the inhibition rate of the composition is directly lower than the inhibition rate of a single compound, and the composition shows an antagonistic effect actually without the synergistic effect.

Comparative Example 4

This embodiment shows that the combination of various monomer compounds and formononetin does not have the synergistic effect. Various monomer compounds are selected from morin, vitexin, apigenin, 3-O-methyl quercetin, kaempferol, dihydromorin, fisetin, naringenin, myricetin, luteolin, kaempferide, baicalein, vincetoxicoside, herbacetin, daidzein, calycosin, phloretin, isoliquiritigenin, cyanidin, and delphinidin.

First, the inhibition rates of various monomer compounds under corresponding concentrations on the α-glucosidase are tested according to the above method, as shown in the following Table 9:

TABLE 9

| Monomer compound | Mass concentration (μg/mL) | Inhibition rate |
|---|---|---|
| Formononetin | 20 | 60.07 ± 5.3% |
| Morin | 1 | 41.2 ± 2.7% |
| Vitexin | 10 | 29.2 ± 1.4% |
| Apigenin | 6 | 56.1 ± 4.4% |
| 3-O-methyl quercetin | 2 | 46.23 ± 1.2% |
| Kaempferol | 2.5 | 40.83 ± 2.3% |
| Dihydromorin | 15 | 25.7 ± 4.7% |
| Fisetin | 6 | 46.5 ± 2.3% |
| Naringenin | 25 | 50.5 ± 4.3% |
| Myricetin | 1 | 41.2 ± 1.5% |
| Luteolin | 1 | 45.5 ± 2.7% |
| Kaempferide | 5 | 30.8 ± 1.3% |
| Baicalein | 10 | 38.8 ± 3.3% |
| Vincetoxicoside | 12 | 48.7 ± 2.1% |
| Herbacetin | 2.5 | 35.2 ± 1.2% |
| Daidzein | 8 | 44.5 ± 2.5% |
| Calycosin | 6 | 56.6 ± 4.3% |
| Phloretin | 8 | 46.3 ± 2.7% |
| Isoliquiritigenin | 4 | 35.2 ± 2.5% |
| Cyanidin | 0.7 | 47.5 ± 1.4% |
| Delphinidin | 1 | 50.2 ± 4.3% |

Then, various monomer compounds and formononetin are combined to test the inhibition rate of the composition on the α-glucosidase, and as shown in the following Table 10:

TABLE 10

| Monomer compound | Monomer compound | Mass concentration ratio | Inhibition rate |
|---|---|---|---|
| Formononetin | Morin | 20:1 | 47.5 ± 2.7% |
| | Vitexin | 20:10 | 49.1 ± 3.3% |
| | Apigenin | 20:6 | 38.6 ± 1.1% |
| | 3-Omethyl quercetin | 20:2 | 59.2 ± 2.5% |
| | Kaempferol | 20:2.5 | 51.3 ± 1.3% |

TABLE 10-continued
| Monomer compound | Monomer compound | Mass concentration ratio | Inhibition rate |
|---|---|---|---|
| | 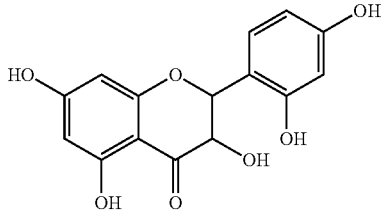 Dihydromorin | 20:15 | 26.3 ± 0.8% |
| | 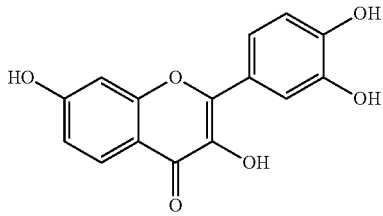 Fisetin | 20:6 | 48.3 ± 2.5% |
| | 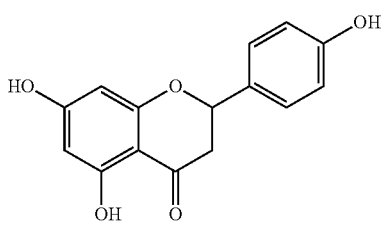 Naringenin | 20:25 | 25.7 ± 1.1% |
| | 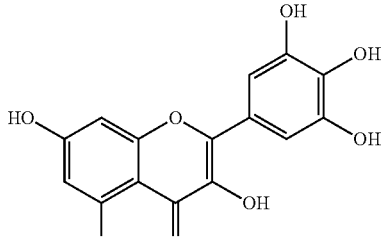 Myricetin | 20:1 | 26.7 ± 0.5% |
| | 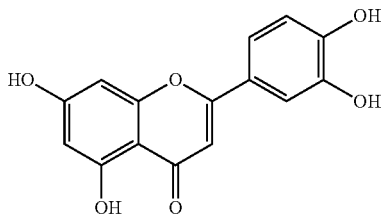 Luteolin | 20:1 | 35.2 ± 1.6% |

TABLE 10-continued
| Monomer compound | Monomer compound | Mass concentration ratio | Inhibition rate |
|---|---|---|---|
| | 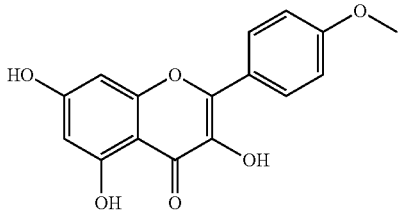 Kaempferide | 20:5 | 43.9 ± 2.2% |
| | 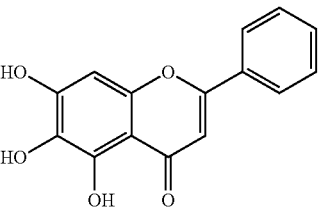 Baicalein | 20:10 | 34.3 ± 1.7% |
| | 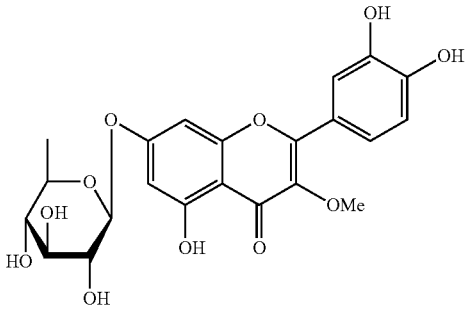 Vincetoxicoside | 20:12 | 22.9 ± 1.2% |
| | 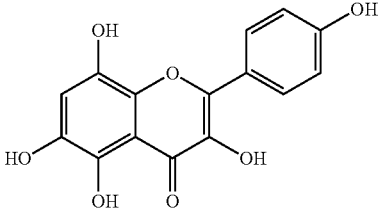 Herbacetin | 20:2.5 | 25.8 ± 0.9% |
| | 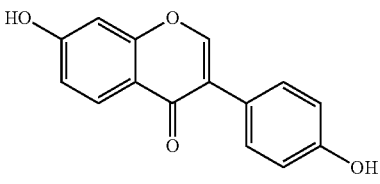 Daidzein | 20:8 | 52.7 ± 3.4% |
| | 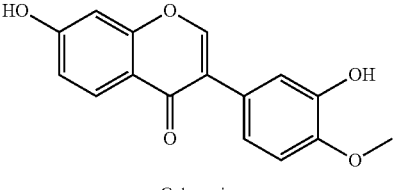 Calycosin | 20:6 | 32.4 ± 1.2% |

TABLE 10-continued

| Monomer compound | Monomer compound | Mass concentration ratio | Inhibition rate |
|---|---|---|---|
| | 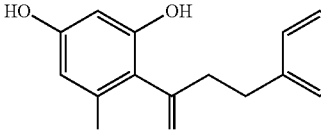<br>Phloretin | 20:8 | 56.5 ± 2.5% |
| | 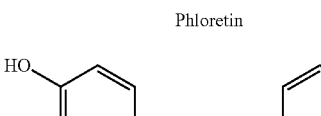<br>Isoliquiritigenin | 20:4 | 54.5 ± 3.1% |
| | 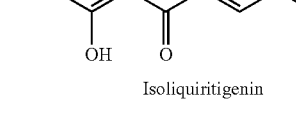<br>Cyanidin | 20:0.7 | 47.1 ± 2.6% |
| | 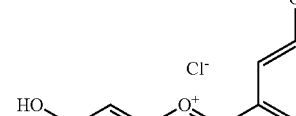<br>Delphinidin | 20:1 | 35.8 ± 1.3% |

As can be seen from Table 10 that after various monomer compounds are combined with the formononetin, the inhibition rate of the composition is directly lower than the inhibition rate of a single compound, and the composition shows an antagonistic effect actually without the synergistic effect.

The above embodiments are merely used for illustration of the technical solutions of the present invention, but not limit them. Although the present invention has been described in detail with reference to the foregoing embodiments, those of ordinary skills in the art should understand that: the technical solutions described in the foregoing embodiments may still be modified, or equivalent substitutions to some of the technical features may be performed. However, these modifications or substitutions do not make the essence of the corresponding technical solutions deviate from the spirit and scope of the technical solutions of the embodiments of the present invention.

What is claimed is:

1. A composition containing hesperetin, wherein the composition contains the hesperetin and a compound X; the compound X is galangin or formononetin;
   a mass ratio of the hesperetin to the galangin is 30:100; and a mass ratio of the hesperetin to the formononetin is 30:20; and
   the composition has a hypoglycemic effect.

2. An α-glucosidase inhibitor, wherein effective components thereof contain hesperetin and galangin or hesperetin and formononetin; a mass ratio of the hesperetin to the galangin is 30:100; and a mass ratio of the hesperetin to the formononetin is 30:20; and the α-glucosidase inhibitor has a hypoglycemic effect.

3. The composition according to claim 1, wherein the hypoglycemic effect is to block digestion and absorption of carbohydrates by inhibiting activity of α-glucosidase to achieve a purpose of controlling postprandial hyperglycemia.

4. A drug having a hypoglycemic effect, wherein effective components thereof contain hesperetin and galangin or hesperetin and formononetin; a mass ratio of the hesperetin to the galangin is 30:100; and a mass ratio of the hesperetin to the formononetin is 30:20; and the drug has a hypoglycemic effect.

5. The drug according to claim 4, wherein the drug contains a carrier, a solvent, a diluent, an excipient, or other mediums acceptable in pharmacy.

6. The drug according to claim 4, wherein a dosage form of the drug is selected from powder, granules, capsules, injection, oral liquid, or tablets.

* * * * *